(12) United States Patent
Karch

(10) Patent No.: US 10,500,322 B2
(45) Date of Patent: Dec. 10, 2019

(54) METHOD AND HEART SUPPORT SYSTEM FOR DETERMINING AN OUTLET PRESSURE

(71) Applicant: Berlin Heart GmbH, Berlin (DE)

(72) Inventor: Dominik Karch, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 213 days.

(21) Appl. No.: 15/322,696

(22) PCT Filed: Jul. 1, 2015

(86) PCT No.: PCT/EP2015/064942
§ 371 (c)(1),
(2) Date: Dec. 28, 2016

(87) PCT Pub. No.: WO2016/001284
PCT Pub. Date: Jan. 7, 2016

(65) Prior Publication Data
US 2017/0128646 A1    May 11, 2017

(30) Foreign Application Priority Data
Jul. 3, 2014   (EP) .................................... 14175698

(51) Int. Cl.
*A61M 1/10*   (2006.01)
*A61M 1/12*   (2006.01)

(52) U.S. Cl.
CPC .......... *A61M 1/1086* (2013.01); *A61M 1/122* (2014.02); *A61M 1/101* (2013.01); *A61M 2205/3331* (2013.01); *A61M 2205/3334* (2013.01); *A61M 2205/3344* (2013.01); *A61M 2205/3365* (2013.01); *A61M 2205/3389* (2013.01); *A61M 2205/3523* (2013.01);
(Continued)

(58) Field of Classification Search
USPC .......................................................... 600/16
See application file for complete search history.

(56) References Cited

U.S. PATENT DOCUMENTS

2003/0045772 A1   3/2003   Reich et al.
2003/0191357 A1*  10/2003  Frazier .................. A61M 1/101
                                                                600/16
(Continued)

FOREIGN PATENT DOCUMENTS

| CN | 1222862 A    | 7/1999 |
| CN | 103857326 A  | 6/2014 |
| EP | 2 298 375 A1 | 3/2011 |

OTHER PUBLICATIONS

English translation of Chinese Office Action issued in CN Patent Application No. 201580036438.8, dated Sep. 5, 2018, pp. 1-5, The State Intellectual Property Office of China, Beijing, CN.
(Continued)

*Primary Examiner* — Nicole F Lavert
(74) *Attorney, Agent, or Firm* — Brinks Gilson & Lione

(57) ABSTRACT

Methods and systems are provided for determining an outlet pressure prevailing at an outlet of a heart assist system. An inlet pressure which prevails at an inlet of the heart assist system may be determined. A pressure difference between the inlet and the outlet of the heart assist system may be determined. The outlet pressure may be determined from the inlet pressure and the pressure difference.

13 Claims, 3 Drawing Sheets

(52) U.S. Cl.
CPC ..... *A61M 2205/50* (2013.01); *A61M 2205/52* (2013.01); *A61M 2205/702* (2013.01)

(56) References Cited

U.S. PATENT DOCUMENTS

2004/0039243 A1    2/2004   Bearnson et al.
2006/0229488 A1   10/2006   Ayre et al.

OTHER PUBLICATIONS

International Search Report with English translation, dated Mar. 18, 2016, pp. 1-4, European Patent Office, Rijswijk, The Netherlands.

* cited by examiner

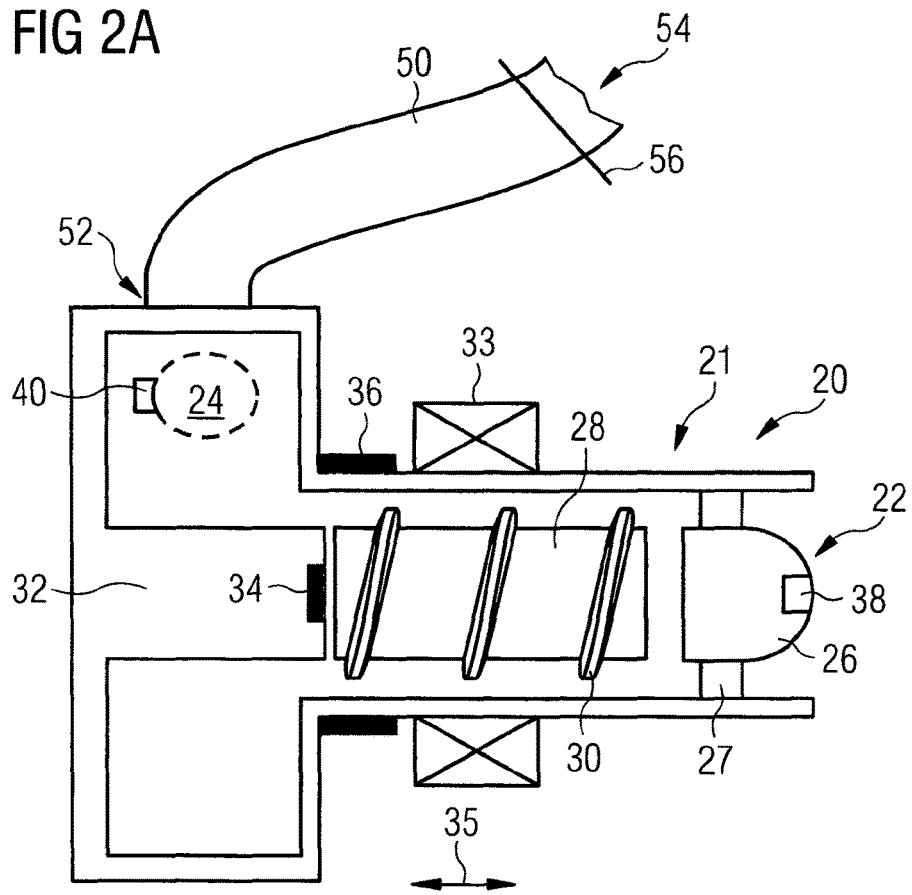
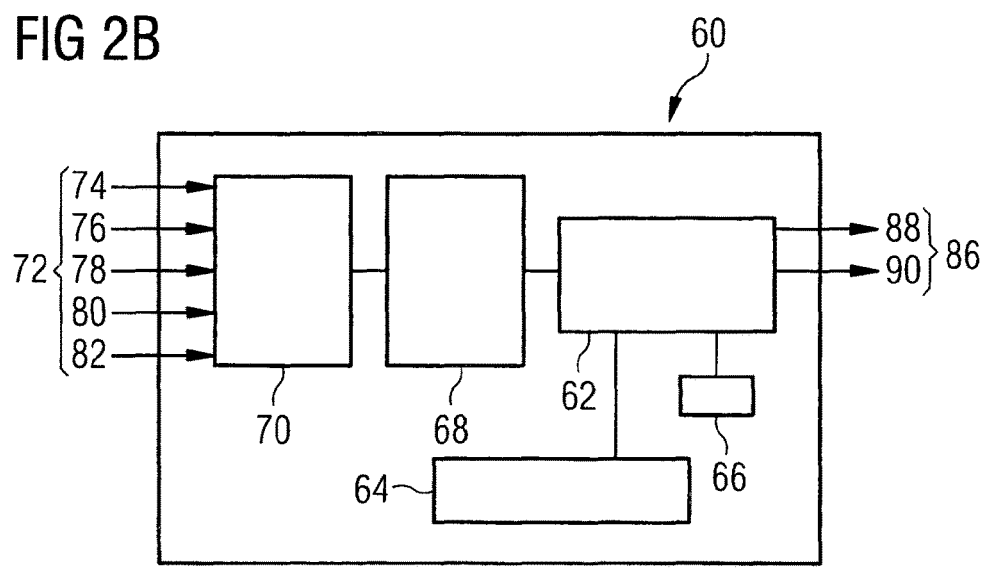

METHOD AND HEART SUPPORT SYSTEM FOR DETERMINING AN OUTLET PRESSURE

CROSS-REFERENCE TO RELATED APPLICATIONS

This application is a 371 nationalization of PCT/EP2015/064942, entitled "A method and a heart assist system for determining an outlet pressure," having an international filing date of Jul. 1, 2015 the entire contents of which are hereby incorporated by reference, which in turn claims priority under 35 USC § 119 to European patent application 14 175 698.1 filed on Jul. 3, 2014, the entire contents of which are hereby incorporated by reference.

TECHNICAL FIELD

The subject-matter of this application is a method for determining an outlet pressure prevailing at an outlet of a heart assist system, to a heart assist system with a pump and with a cannula connectable to the pump, as well as a method for operation of a heart assist system in a human body.

BRIEF DESCRIPTION OF THE DRAWINGS

FIG. 2a an exemplary construction of a pump with a cannula connected thereto;
FIG. 2b a schematic construction of a control unit of the heart assist system,
FIG. 3 a schematic procedural diagram for a method for determining an outlet pressure prevailing at an outlet of a heart assist system.

DETAILED DESCRIPTION

Figure 1:
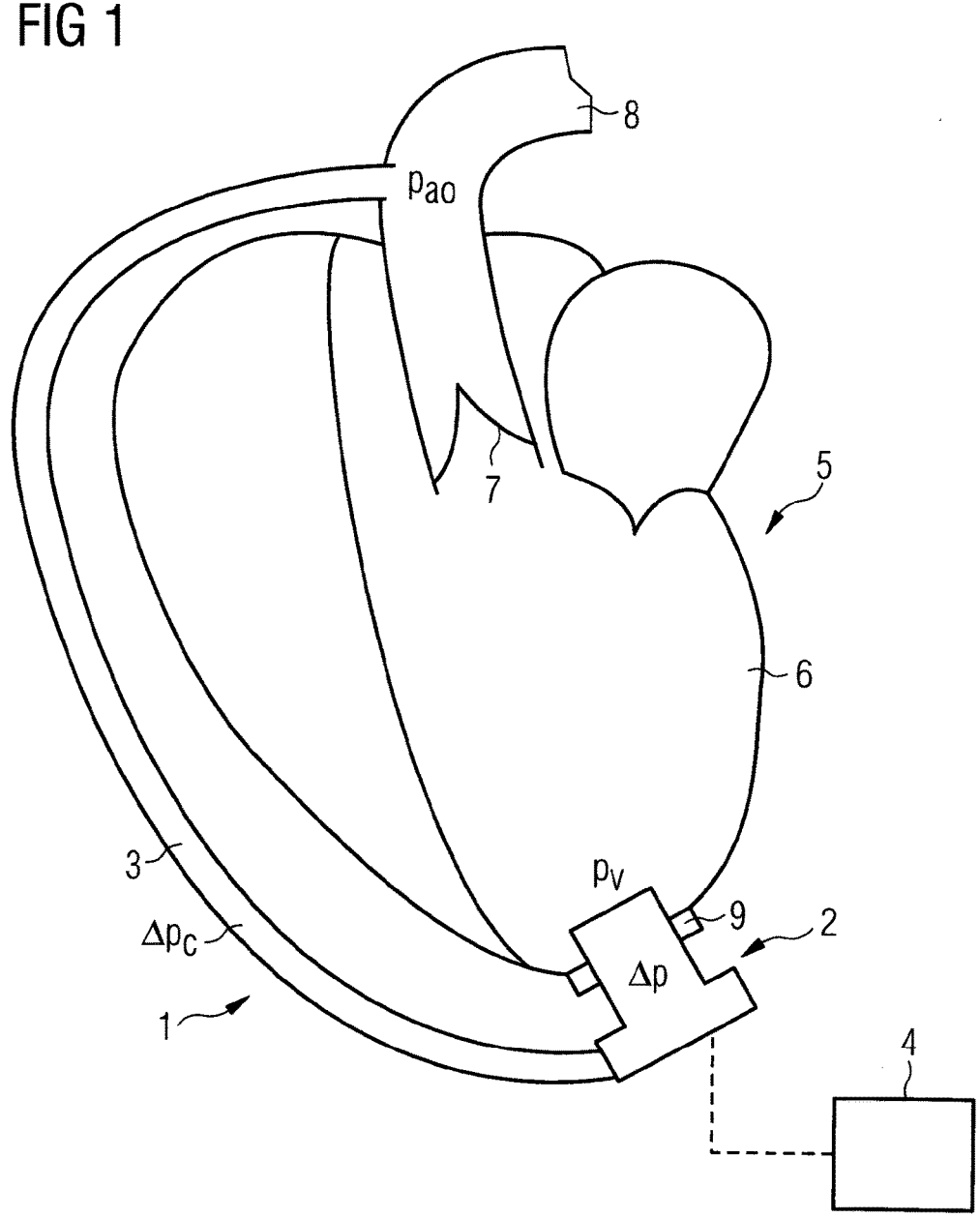
FIG. 1 a schematic construction of a heart assist system.

The heart assist systems which are specified in this application are so-called ventricular assist devices (VAD). These can be designed for the left ventricle (LVAD), the right ventricle (RVAD) or both ventricles (BVAD). The subject-matters of this application are predominantly described hereinafter in the context of LVADs, although the respective pumps can also be applied as RVADs or BVADs.

When operating a heart assist system as an LVAD, the heart assist system is connected mostly to the left ventricle and the aorta whilst bypassing the aortic valve. A bypass is thus applied which can pump blood through the heart assist system from the left ventricle into the aorta. In numerous cases, the heart assist system comprises a pump unit as well as an inlet and outlet cannula. Other variants envisage coupling the pump unit directly onto the heart and pumping the blood delivered by the pump unit from the pump outlet to the aorta by way of a cannula. Suitable pumps are here rotating blood pumps which can either be designed as axial pumps or radial pumps. The axial pumps are pumps which deliver the blood axially, i.e. deliver the blood by way of a predominantly axial advancing force. The pumps for the axial delivery of the blood can be connected to a radial outlet. In contrast to the axial pumps, radial pumps comprise rotors which apart from subjecting the blood to an axial component also subject it to a radial component. In many cases, the rotor expands radially, so that the rotor diameter at the pump inlet is mostly smaller than the rotor diameter in the proximity of the pump outlet. Radial pumps are sometimes also called turbo pumps.

Data is continuously acquired or detected in order to measure the delivered blood quantity and prevailing pressures, so as to ensure a reliable operation of the heart assist system for the patient.

One possibility of measuring the pressures which are relevant to heart assist systems lies in providing absolute pressure sensors in the heart assist system. Relevant pressures in an LVAD system here, amongst others, are the ventricle pressure $p_v$, and the aortic pressure $p_{ao}$. It may be envisaged to measure the ventricle pressure directly in the ventricle in order to measure the ventricle pressure. With heart assist systems with which the pump unit is connected directly to the ventricle, a pressure measured at the pump inlet can be essentially equated with the ventricle pressure. The measurement of the aortic pressure is more difficult to achieve. In a variant, a pressure sensor can be arranged for example in the aorta. The anchoring of a sensor, however, is quite difficult due to the pressures, the flow speeds and the difficult accessibility of the aorta, and entails a significant health risk.

In view of this, there exists the need to determine the aortic pressure or the pressure at the exit of a heart assist system in a different manner.

According to a method for determining an outlet pressure prevailing at an outlet of a heart assist system, an inlet pressure prevailing at an inlet of the heart assist system is first determined. The determining of the inlet pressure can be effected for example by way of a pressure sensor which is arranged at the inlet of the heart assist system. A pressure sensor which is separate from the heart assist system, as is applied for example in heart pacemaker systems or implantable defibrillator systems, can alternatively be used. The acquired pressure data can then be relayed, in a wireless manner for example, to a control unit of the heart assist system.

A pressure difference prevailing between the inlet and the outlet of the heart assist system is estimated in order to determine the outlet pressure. In particular, this means that part-sections of the heart assist system can be measured or estimated. The estimation of a pressure difference between the inlet and the outlet of the heart assist system can thus be understood in that at least a pressure drop across a part-section of the heart assist system is estimated. The term "estimation" is here to be understood in a manner such that the pressure drop or the pressure difference is determined by way of variables which are not directly measured in this section.

In an embodiment, the heart assist system for example comprises a pump with a pump inlet and with a pump outlet, and further comprises a cannula with a cannula inlet and with a cannula outlet, wherein the pump outlet is connected to the cannula inlet. The pressure difference between the inlet and the outlet of the heart assist system is here composed of a pump pressure difference between the pump inlet and the pump outlet, and of a cannula pressure difference between the cannula inlet and the cannula outlet. The cannula connects the pump to the aorta and for example can comprise a biocompatible material, such as silicone or a graft material, or be formed from this material. The final length of the cannula is often not known until after the implantation due to the fact that the cannulae often need to be individually adapted to the patient on implantation, i.e.

the cannulae are possibly shortened during implantation. The cannula pressure difference can be estimated with the help of parameters or variables which are measured by way of the pump, with the help of the methods and the heart assist system described in this application. The outlet pressure can be subsequently determined from the inlet pressure and from the estimated pressure difference once the pressure difference between the inlet and the outlet of the heart assist system has been estimated.

Alternatively, it may be envisaged to attach a pressure sensor for determining the aortic pressure at the outlet of the heart assist system connected to the aorta. Now if a pressure sensor were to be arranged at the outlet of the cannula, it would be liable to be removed due to a necessary shortening of the cannulae. A pressure sensor can alternatively be arranged within the cannula, however, the pressure measured in the cannula may differ from the aortic pressure, so that again a pressure drop of the cannula section between the pressure sensor and the cannula outlet should be estimated in this case.

A heart assist system according to this application comprises a pump and a cannula connectable to the pump. The heart assist system moreover comprises a pressure detection system which is configurable in a manner such that a pressure prevailing at the pump inlet is detectable and that a pump pressure difference between the pump inlet and the pump outlet is detectable, and that a control unit is present which is configured in a manner such that a cannula pressure difference between the cannula inlet and the cannula outlet can be estimated. As already mentioned, the estimation of the cannula pressure difference can be carried out on the basis of variables which are detectable by the pump, its pressure detection system and further sensor means of the pump.

Here, the control unit, which can be designed, for example, as a microprocessor, a microcontroller or a programmable field array, is equipped with a command set or a software with instructions which outputs an estimated value of the cannula pressure difference by way of the reading detected by the pump and by way of a model for estimating the cannula pressure difference. The commands or the software or firmware can here be kept in a memory unit and/or can be provided and transmitted onto a control unit by way of a data carrier such as a CD, a DVD, a transportable flash memory. The control unit is configured in a manner such that the cannula pressure difference is computed from variables determined by way of the pump on the basis of the model concerning the cannula pressure difference and of calibrated model parameters belonging to the model. The control unit moreover in some embodiment examples comprises commands for carrying out a method for calibrating the model parameters.

In an embodiment, the model for estimating the cannula pressure difference, as independent variables can comprise one or more of the following variables detectable by the pump: volume flow, rotation speed of the pump or the pump pressure difference between the pump inlet and the pump outlet. The cannula pressure difference or the cannula outlet pressure can be estimated as a dependent variable.

It may be envisaged to calibrate parameters of the model by way of measurement data in order to adapt a model for estimating the cannula pressure difference to a patient. The model parameters can herein be modelled for example by way of statistical methods such as regression analysis, for example. The modelling of the parameters can herein be carried out during continuous operation of the pump, the parameters can be calibrated at regular maintenance intervals, or the model parameters can be calibrated once, for example shortly after the implantation. The calibration of the model parameters herein can either be carried out by the control unit or by way of a further, external control unit. The model parameters can be modelled in a time-independent or time-dependent manner. In the case that the calibration is a one-time calibration or is repeated at regular intervals, the model parameters determined by way of statistical methods are stored in a memory connected to the control unit, for example in a RAM or ROM, and used for determining the cannula differential pressure.

As already mentioned initially, the cannula pressure difference can be estimated by way of different variables detectable by the pump. Thus for example in a first variant, one can envisage estimating the cannula pressure difference at points in time, at which the aortic valve is opened, in particular at points in time shortly after the opening of the aortic valve and before the closure of the aortic valve. As an approximation, the cannula pressure difference is equal to the pump pressure difference at these points in time. Apart from the point in time of the opening of the aortic valve, no further parameters need to be determined for this first variant. However, the disadvantage with this method is the fact that the estimation is only satisfactorily accurate at few points in time (shortly after the opening of the aortic valve).

In a second variant, it may be envisaged to estimate the cannula pressure difference with the help of the volume flow delivered by the pump. Thus, for example, the cannula pressure difference can be estimated over a physiological meaningful region by way of a model of a non-linear function, such as a polynomial or exponential function for example, or of a linear function. Here, the volume flow, the rotational speed of the pump, the pump pressure difference or combinations of these variables, or variables proportional to these variables, can serve as an independent variable. Thus, for example, a polynomial or an exponential function of the pump differential pressure and of the speed of the rotor can be used for estimating the cannula pressure difference. Moreover, with some pumps of the state of the art for example, it is possible to determine the pump pressure difference by way of a current applied to a control coil, wherein the control coil determines a position of a pump rotor. Since the position is changed on account of the prevailing pressure and prevailing volume flow by way of the delivered fluid, the current flowing through the control coil is proportional to the pump pressure difference.

In a third variant, the model of the cannula pressure difference can comprise a differential equation or a differential equation system.

Here, common to the second and third variant is the fact that the model comprises model parameters which are determined, for example, from measurement data by way of statistical methods. Exemplary methods for calibrating the models can be found in the embodiment examples.

In a further embodiment of the heart assist system, this comprises a volume flow sensor. The volume flow can be determined in a direct manner by way of the volume flow sensor. An ultrasound flow sensor, a Prandtl probe, an orifice flowmeter or a magnetically inductive flow sensor for example can be used as a flow sensor. A pump system for the indirect measurement of the volume flow, for example by way of a displacement of a rotor, does not fall under the term of a volume flow sensor.

In a further embodiment, the pressure detection system comprises a pressure sensor at the pump inlet, and a pressure sensor at the pump outlet. The pump differential pressure can be determined by way of these absolute pressure sensors. A pressure sensor which is arranged at the pump inlet for example is suitable for determining the ventricle pressure of a heart assist system. Alternatively or supplementary to a sensor at the pump inlet and/or outlet, a pump system for determining a differential pressure can be present. Such a system can be formed for example by way of a system for detecting and compensating a pump rotor offset. For this, a family of characteristics is required which brings the respective current for displacing the pump rotor which is flowing through at least one control coil of the system into relation with the respective pressure difference or volume flow.

Further embodiment examples can be found in the examples specified hereinafter.

FIG. 1 shows the schematic construction of an implantable heart assist system 1. The exemplary heart assist system 1 comprises a pump 2 which at its outlet is connected to a cannula 3. The pump unit or the pump 2 may be an axial pump as well as a radial pump. The pumps can be set, for example by way of the control unit 4, in a manner such that they deliver a defined quantity of blood. Other delivery programs, however, are also possible, such as a delivery type which imitates the beat of a natural heart more precisely.

The cannula 3 can be formed for example of silicone or a softer graft material, such as for example a polyester, ePTFE or mixtures of these materials. The control unit 4 can either be fastened completely to the pump 2, partly to the pump 2 or arranged completely remotely from the pump unit 2. The control unit 4 can comprise electronic or electrical control elements such as of example a processor, memory, signal processing circuits, motor control circuits as well as monitoring systems.

The represented pump 2 is an axial pump which is coupled with its inlet directly onto a heart 5. In the present example the heart assist system is an LVAD system. The left ventricle 6 is physiologically connected to the aorta 8 via the aortic valve 7. The heart assist system 1 represents a bypass from the left ventricle 6 to the aorta 8. With an RVAD system, the pump would be connected to the right ventricle and to the pulmonary artery, and with a BVAD system a double chamber pump would be provided which forms an LVAD system with the first chamber and forms an RVAD system with the second chamber. Alternatively, two pumps can be present.

In the present example of an LVAD system, blood is delivered from the left ventricle 6 through the pump unit 2 and the cannula 3, wherein the outlet of the cannula 3 is connected to the aorta 8. Furthermore, a suture ring 9 with which the pump 2 is fastened to the apex of the heart is represented in FIG. 1.

A ventricle pressure $p_v$ prevails in the left ventricle 6, and an aortic pressure $p_{ao}$ prevails in the aorta. Seen physiologically, the aortic valve 7 opens when the pressure $p_v$ in the ventricle is larger than the aortic pressure $p_{ao}$. The aortic pressure $p_{ao}$ can be described as the sum of the ventricle pressure $p_v$, of the pressure drop $\Delta p$ across the pump 2, as well as the pressure drop $\Delta p_c$ across the cannula 3, i.e.

$p_{ao}=p_v+\Delta p+\Delta p_c.$

One option for determining the aortic pressure would be, for example, to place an additional pressure sensor in the aorta 8. However, the implantation entails a certain health risk. Alternatively to this, a pressure sensor for detecting the pressure at the outlet of the cannula can be arranged on or in the outlet of the cannula 3 which is connected to the aorta 8. Although this variant permits direct measurement of the aortic pressure, the sensor arranged in the cannula requires a data connection to the control unit 4. Due to the fact that the cannula 3 often needs to be shortened or is shortened on implantation connected to the aorta 8 only afterwards, it cannot be ensured that a pressure sensor arranged at the outlet of the cannula 3 is still present after cutting the cannula to size. One possible solution here is to displace the pressure sensor into the cannula 3. In this case, however, at least the pressure drop between the location of the sensor and the outlet of the cannula 3 which is connected to the aorta 8 must be estimated.

The method which is presented in this application is based on a possibility of determining the aortic pressure $p_{ao}$, for example by way of estimating the pressure drop $\Delta p_c$. If the further variables, i.e. $p_v$ and $\Delta p$, can be detected by measurements, then the aortic pressure can be determined from the measured variables of the ventricle pressure and the pressure drop over the pump. Although the heart assist system 1 in FIG. 1 only has an outlet cannula, the heart assist system can also comprise an inlet cannula. The methods presented here can also be applied with such a heart assist system.

An exemplary heart assist system 20 is represented in more detail in FIG. 2a. The heart assist system comprises a pump 21 with a pump inlet 22 and with a pump outlet 24. The pump unit pumps blood from the pump inlet 22 past inlet guide vanes 26, which are connected to a casing wall of the pump 21 via vanes 27, to a delivery element 28 which is designed, for example, as a rotor. The delivery element 28 in the present example comprises a spiral 30 which delivers the blood towards the outlet guide element 32. The delivery element 28 is herein brought into rotation by way of a motor 33. For this, permanent magnets which can be brought into rotation by the motor current of the motor 33 are located in the delivery element 28. The outlet guide vanes, which is to say the outlet guide element 32, are arranged in a spiral chamber, into which the axially delivered blood is delivered and is subsequently pressed through the pump outlet 24.

Examples for such pumps can be learned, among others, from the documents WO 2013/021014, WP 2012/150045, WO 2012/149946, WO 2011/054545 and WO 02/066837, which are incorporated as a constituent of this application in their entirety. Further exemplary pumps are disclosed, for example, in WO 2012/051454 or WO 2012/024493.

In the present example, the pump 21 comprises a pressure detection system. This for example comprises a sensor coil 34 which can detect a distance of the delivery element 28 to the outlet guide body 32. If a force directed along the directions 35 acts upon the delivery element 28 on account of the delivered blood flow, then this delivery element is deflected out of an idle position and a current is induced on the sensor coil 34 by way of this. This induced current is detected and is processed in the control unit or another circuit in a manner such that the delivery element 28, by way of subjecting a control coil 36 to current, is brought again into a position between the inlet guide vanes 26 and the outlet guide body 32 which corresponds to the idle position. A pressure difference between the pump inlet 22 and the pump outlet 24 can be determined for example by way of the current prevailing at the control coil 36 (measured directly or indirectly).

The pressure detection system can moreover comprise a pressure sensor 38 which is arranged at the inlet 22 of the pump 31. This pressure sensor detects the blood pressure at the inlet of the pump, so that for example a ventricle pressure $p_v$ can be determined, as is shown in FIG. 1. The pressure detection system can moreover comprise a further pressure sensor 40 which detects the pressure at the outlet 24 of the pump. If the pump comprises two sensors at the inlet and outlet, then the pump pressure difference can be determined from the two measured values. At least one of the two pressure sensors however can also be replaced or supplemented by a differential pressure sensor system, for example such as the system, which comprises the elements 34 and 36, for the indirect detection of the differential pressure of the pump. The various data detected with the help of the pressure detection system are acquired by a control unit, processed and used for estimating the aortic pressure.

The heart assist system 20 moreover comprises a cannula 50, which is manufactured for example of a silicone. A cannula inlet 52 is here connected to the pump inlet 24, for example via a snap-fit connector. The cannula 50 can be connected, for example sewn, to the aorta at the cannula outlet 54. It may be necessary to shorten the cannula, for example to a length 56, before connecting the aorta to the cannula. For this reason, it is envisaged to not provide any active sensory means in the cannula in some embodiment examples. However, the system which is presented here, and the method presented here, can also be used to complement active sensory means in the cannula.

If no sensor components are present in the cannula, then the pressure drop between the cannula inlet 52 and the cannula outlet 54 or the shortened cannula outlet 56 can also be estimated with the help of a method which is explained in this application. Estimating here is to be understood in that it is only possible to fall back on variables determined by way of the pump 21 or on variables measured outside the pump or cannula when determining the pressure drop $\Delta p_c$ along the cannula 50. Different models for estimating the cannula pressure drop or cannula pressure difference are possible for this.

An exemplary control unit 60 is represented schematically in FIG. 2b. The control unit 60 can be arranged, for example, in an external casing outside the body. Data which is detected by the pump unit is transferred to the control unit 60 for example via a data bus. However, the control unit may also be fastened to the pump unit, for example integrated into a pump casing. The control unit represented here comprises a CPU 62 which is configured for the operation of the heart assist system. This means that it is in particular capable of setting the speed of the heart assist system.

The CPU 62 is connected to a first memory unit 64 in which a variety of commands and control programs are stored. In the present example, the control commands also comprise instructions for determining the estimated aortic pressure and instructions for determining model parameters of a model for aortic pressure estimation or cannula pressure difference estimation. The CPU 62 can moreover be connected to a further memory 66 which for example is configured by a user, for recording data and for the data to be read out at a later stage.

Connected in front of the CPU is a signal-processing stage 68 which filters and processes incoming signals arriving at the data input 70, so that the data can be processed by the CPU 62. Apart from filters, the signal processing stage 68 can comprise, for example, analog/digital converters or the like.

Signals 72 arrive at the data input 70. These signals for example comprise measured motor currents 7 for determining the speed, signals of the absolute pressure sensor 38 in the form of the signals 76 and further signals 78 representing signals of the absolute pressure sensor 40. Signals 80 represent the current which prevails in the control coil 36 and which can be converted by the CPU 62 into a pump differential pressure. The pump system represented in FIG. 2a may optionally also comprise a volume flow sensor, whose signals 82 are likewise entered at the data input 70. The CPU 62 can moreover transmit signals back to the pump, such as for example the signals 86, which are represented by way of example as activation currents 88 for the motor or currents for the control coil 36.

Figure 3:
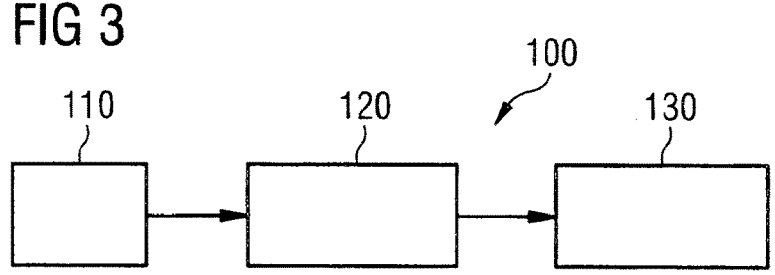

A method for determining the aortic pressure (also called after-load of the heart assist system) shall now be explained by means of FIG. 3. The method 100 for determining the aortic or outlet pressure of the heart assist system comprises the step 110, in which firstly a pressure in the ventricle or at the heart assist system inlet is measured. This measurement can be carried out for example by way of an absolute pressure sensor at the inlet of the heart assist system. Subsequently, a differential pressure between the inlet and the outlet of the heart assist system is estimated with the help of a calibrated model. This is effected in step 120. The aortic pressure or outlet pressure can be determined in step 130, from the estimated pressure difference and the measured inlet pressure.

Figure 4:
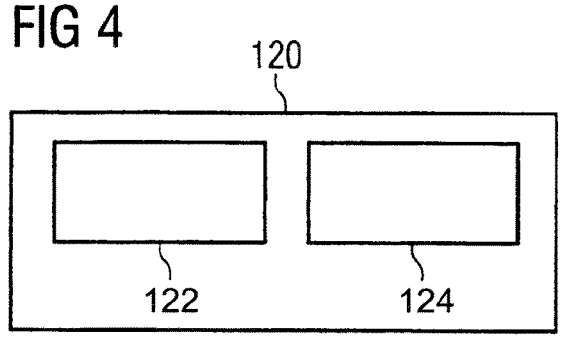
FIG. 4 a schematic representation of the estimation of the pump pressure difference of a heart assist system with a pump and with a cannula.

In the case of a heart assist system with a pump and with a cannula connected thereto as illustrated in FIG. 4, the step 120 can be divided into individual steps in such a manner that a pump pressure difference is first measured in step 122 and a cannula pressure difference is subsequently estimated by way of the variables measured with the help of the pump and by means of a model of the cannula pressure difference (step 124).

Figure 5:
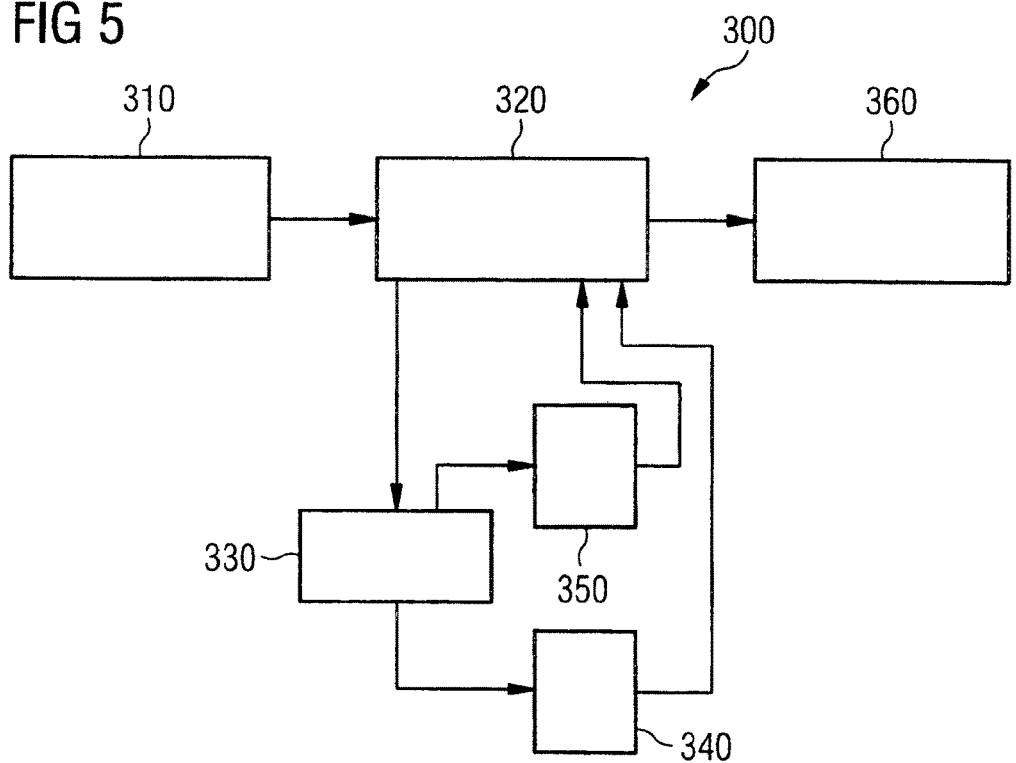
FIG. 5 a schematic overview concerning a method for determining model parameters for a model for determining the cannula pressure difference.

By means of FIG. 5, different models of the cannula pressure difference will now be explained, possibilities for calibrating or determining the respective model parameters will be specified, and it will be explained as to how the model calibrated with the model parameters is to be applied in the heart assist system.

The exemplary method 300 firstly comprises the evaluation of a model of the cannula pressure difference 310. Here, different models can be considered. Some models shall be cited here by way of example.

In a first model, the cannula pressure difference $\Delta p_c$ can be modelled by the pump pressure difference $\Delta p$ at selected points in time. Thus it is known, for example, that the ventricle pressure $p_v$ briefly is essentially the same as the aortic pressure $p_{ao}$ at the point in time of the opening of the aortic valve. For these points in time, the model can therefore be set up such that the cannula pressure difference is the same as the pump pressure difference. This model, however, is only applicable at few points in time during an individual heart cycle, since the differences between the aortic pressure and the ventricle pressure significantly differ from one another at other points in time than at the point in time of the opening of the aortic valve. That is, the points in time at which the model is valid need to be continuously determined and in this context form the model parameters. A method which can reliably determine the opening, and in particular the point in time of the opening of the aortic valve, is necessary for this. A time interval, beginning with the opening, in which the model is applied is the last thing to be subsequently determined. If the pump or its control unit is in the position of determining the opening of the aortic valve, a control unit of a heart assist system can determine the aortic pressure at least at the points in time of the opening of the heart valve. However, the disadvantage of the model is the fact that a continuous determining of the aortic pressure does not provide satisfactory results.

A further model for determining the cannula pressure difference is a relationship between a static volume flow which can be determined for example by way of variables able to be determined by way of the pump. The pressure difference $\Delta p_c$, for example, can be approximated by a non-linear function. Here, a polynomial of the third order of the volume flow is cited as one example. However, other non-linear functions, such as an exponential function for example, may alternatively also be applied. The polynomial can be represented as follows:

$$\Delta p_c = k_3 \dot{Q}_p^3 + k_2 \dot{Q}_p^2 + k_1 \dot{Q}_p^1,$$

wherein $\dot{Q}$ represents the volume flow through the pump, and the model parameters $k_1$, $k_2$, $k_3$ must be determined.

In order to determine model parameters $k_1$, $k_2$, $k_3$, it is envisaged in one embodiment that the pressure drop $\Delta p_c$ over the cannula is known at certain measurement points, the volume flow is approximately constant and at least three different measurement points are known. However, once the model parameters are determined or calibrated, the model can be applied for the continuous estimation of the cannula pressure difference, i.e. the method also provides satisfactory results in the portions of the heart cycles with a closed aortic valve. Here, it is advantageous that the calibration of the model only needs to be effected once, wherein a calibration can be carried out at defined, for example regular, time intervals, such as days, weeks or months.

As already described in the first model, the pressure drop in the cannula $\Delta p_c$ is essentially equal to the pressure drop in the pump, at least at points in time briefly after the opening of the aortic valve. The cannula pressure difference can therefore be determined at least for these points in time. The pressure difference between the ventricle and the aorta is approximately constant at these points in time. Volume flows through the aortic valve and through the pump are therefore also approximately constant. Since the volume flow during the ejection phase of the ventricle, although being approximately constant, is however not absolutely constant, limit values can be set by way of which it is determined that the volume flow drop during the ejection (expulsion) phase of the heart is constant to a satisfactory extent. For example, the standard deviation of the volume flow during the ejection phase can be determined here and a limit value can be set below which the ejection phase interval can be applied for determining the model parameters.

In order to furthermore be able to determine the parameters for a large speed range of the pump, measurements are carried out at several, for example three, different rotation speeds n, and the associated data or time series are recorded. The model parameters $k_1$, $k_2$, $k_3$ are then determined for the time series of the pump pressure difference and of the volume flow through the pump recorded during the respective rotation speed, in combination with the criteria that the volume flow is constant to a satisfactory extent and the cannula pressure difference can be essentially equated with the pump pressure difference. Here, the following relation may, for example, be applied:

$$\vec{k} = \Delta p(\vec{t}) \cdot \hat{Q}+(t)$$

Here, $\hat{Q}^+$ is the pseudo-inverse of the matrix $\hat{Q}$, which as entries has values $\dot{Q}_p^3$, $\dot{Q}_p^2$ and $\dot{Q}_p^1$ recorded at different measuring points in time. Whilst the k-vector is three-dimensional in this embodiment example, the pump pressure difference vector is m-dimensional, provided that m measuring points are present. The matrix $\hat{Q}$ is an [mx3] matrix. The parameters $k_1$, $k_2$, $k_3$ can therefore be determined and validated by way of statistical methods, such as a regression for example. Once the model parameters $k_1$, $k_2$, $k_3$ have been determined, the cannula pressure difference can be estimated by the model, with the help of the volume flow flowing through the pump, at any points in time of the heart cycle.

Thus, first of all the points in time of the opening of the aortic valve are determined at different speeds in step 330. The respective measurement data of the volume flow and of the pump pressure difference is acquired in the steps 340 and 350. A calibration of the model parameters, e.g. an evaluation of the model parameters with the desired precision is subsequently carried out from the detected data, under the described marginal conditions, so that the model parameters are calibrated in step 320. The model can be subsequently applied by the control unit (step 360), so that an assertion concerning the pump outlet pressure or cannula outlet pressure, which almost corresponds to the aortic pressure, can be made by way of measuring the volume flow, the pump pressure difference and the pump inlet pressure.

A further model is the use of a differential equation system for determining the cannula pressure difference. Whereas the model described in the preceding section was modelled essentially on a static cannula pressure difference, a dynamic cannula pressure difference term can also be determined by a differential equation. One possibility of modelling the cannula pressure difference $\Delta p_c$ for example is:

$$\Delta p_c = L_c \frac{d\dot{Q}_p}{dt} + R_c(\dot{Q}_p) \cdot \dot{Q}_p,$$

wherein $R_c(\dot{Q}_p) \cdot \dot{Q}_p$ can correspond to the static cannula pressure difference term of the second variant ($R_C$ corresponds to a resistance term of an equivalent circuit diagram) and $L_c$ models a mass inertia of the fluid volume of the cannula and of the pump. The mass inertia of the fluid volume in the pump can be determined by way of the geometry of the pump. The mass inertia $L_c^*$ of the fluid volume of the cannula, for example with a cannula which is round in its inner cross section and has a length l, can be defined by the term $$L_c = \frac{4\rho l}{\pi D_i^2},$$

wherein $\rho$ is the density of the blood, l the length of the cannula and $D_i$ the diameter of the cannula. Other geometries of a cannula can be included by way of adapting the mass inertia term (e.g. by way of integration over all part sections of the cannula) and are evident to the person skilled in the art. The mass inertia for known cannulae can also be determined experimentally as a numeric value.

Similarly to the preceding case, with application of this model one can proceed by way of the static parameters $k_1$ to $k_3$ being determined first. Subsequently, for example the length of the cannula and its known inner diameter are determined and transmitted to the control unit. The cannula pressure difference can then be estimated on the basis of the collected information.

Furthermore, as an extension of these models, the pressure drop over the aortic valve may be integrated. This pressure drop can e.g. be estimated on the basis of an assumed geometry of the aortic valve or of a geometry of this which is measured by way of imaging methods.

The influence of the elasticity of the cannulae has moreover been ignored in the previously represented models, since the cannulae have a high elasticity and thus no wave reflections are to be expected in the frequency range of interest. However, it is conceivable to include a term for the elasticity of the cannula in the region of the aortic anastomosis, into the models, and this could possibly improve the accuracy of the estimation.

Although the models for determining the cannula pressure difference presented here have only been models which contain the volume flow as an independent variable, similar models can also be set up for a pump pressure difference or a rotation speed or a combination of these variables.

Once a model for the cannula pressure difference has been created, the outlet pressure or aortic pressure can be determined from the pump inlet pressure or ventricle pressure, the pump pressure drop and the model.

It should be noted that it is very simple for the person skilled in the art to determine embodiment examples which likewise fall under the protective scope of the application once these disclosures have been revealed.

The invention claimed is:

1. A heart assist system comprising:
a pump for assistance of a heart;
a cannula which is connectable to the pump, wherein the pump comprises a pump inlet and a pump outlet, and the cannula comprises a cannula inlet and a cannula outlet;
a pressure detection system configured to detect a pressure at the pump inlet, which represents a ventricle pressure of a ventricle of the heart, and a pump pressure difference between the pump inlet and the pump outlet; and
a control unit configured to estimate a cannula pressure difference between the cannula inlet and the cannula outlet, which represents a pressure difference along a bypass running between the ventricle and an aorta of the heart, and the control unit is configured to determine an aortic pressure from the pressure at the pump inlet representing the ventricle pressure and from the cannula pressure difference.

2. The heart assist system according to claim 1, wherein the control unit comprises a microprocessor, a microcontroller, a programmable field array, or an external control unit.

3. The heart assist system according to claim 1, wherein the control unit comprises a memory unit, and the memory unit is configured to store commands and/or parameters for estimating the cannula pressure difference.

4. The heart assist system according to claim 1, wherein the control unit is connected to the pressure detection system so that data detected by the pressure detection system is transferable to the control unit.

5. The heart assist system according to claim 1 further comprising a volume flow sensor.

6. The heart assist system according to claim 1, wherein the control unit is configured to estimate the cannula pressure difference based on at least one variable detected by the pump.

7. The heart assist system according to claim 6, wherein the control unit is configured to determine the cannula pressure difference based on a volume flow through the pump.

8. The heart assist system according to claim 7, wherein the control unit is configured to determine the volume flow based on the pump pressure difference.

9. The heart assist system according to claim 1, wherein the pressure detection system comprises a pressure sensor at the pump inlet, a pressure sensor at the pump outlet, and/or a differential pressure sensor in the pump.

10. The heart assist system according to claim 8, wherein the pump pressure difference is determined based on a displacement of a pump rotor.

11. The heart assist system according to claim 1, wherein the control unit is configured to determine a model of the cannula pressure difference, wherein at least one parameter of the model is determined based on a statistical method.

12. The heart assist system according to claim 1, wherein the control unit is configured to estimate the cannula pressure difference based on a higher order polynomial that is a function of a variable measurable by the heart assist system.

13. The heart assist system according to claim 1, wherein the pressure at the pump inlet represents the ventricle pressure of a left ventricle of the heart, and the cannula pressure difference represents the pressure difference along the bypass running between the left ventricle and the aorta of the heart.

* * * * *